United States Patent [19]

Engelhardt et al.

[11] Patent Number: 5,613,967
[45] Date of Patent: Mar. 25, 1997

[54] APPARATUS FOR MAINTAINING BONE PORTIONS IN A DESIRED SPATIAL RELATIONSHIP

[75] Inventors: John Engelhardt, Chagrin Falls; Alexandre M. Dinello, Shaker Heights, both of Ohio

[73] Assignee: AcroMed Corporation, Cleveland, Ohio

[21] Appl. No.: 431,124

[22] Filed: Apr. 28, 1995

[51] Int. Cl.⁶ .................................................. A61B 17/56
[52] U.S. Cl. ................................ 606/61; 606/69; 606/73; 606/71
[58] Field of Search ........................ 606/60, 61, 69, 606/70, 71, 72, 73

[56] References Cited

U.S. PATENT DOCUMENTS

| | | | |
|---|---|---|---|
| 4,653,481 | 3/1987 | Howland et al. | 606/61 |
| 4,854,311 | 8/1989 | Steffee | 606/73 |
| 5,085,660 | 2/1992 | Lin | 606/69 |
| 5,129,889 | 7/1992 | Small et al. | 606/61 |
| 5,290,288 | 3/1994 | Vignaud et al. | 606/61 |

FOREIGN PATENT DOCUMENTS

| | | |
|---|---|---|
| 0506420 | 9/1992 | European Pat. Off. . |
| 9111967 | 8/1991 | WIPO . |
| 9406361 | 3/1994 | WIPO . |

*Primary Examiner*—Michael Powell Buiz
*Assistant Examiner*—Mark S. Leonardo
*Attorney, Agent, or Firm*—Tarolli, Sundheim, Covell, Tummino & Szabo

[57] ABSTRACT

An apparatus for retaining bone portions in a desired spatial relationship includes a longitudinal plate extendable along the bone portions. A fastener has a first end portion engageable with a bone portion. A connecting member for connecting the plate to the fastener in any one of an infinite number of positions along the slot includes a recess for receiving a portion of the plate. The recess has an interference fit with the portion of the plate received in the recess. A nut engages the second end portion of the fastener to apply a force to cause the interference fit between the plate and the recess.

35 Claims, 2 Drawing Sheets

APPARATUS FOR MAINTAINING BONE PORTIONS IN A DESIRED SPATIAL RELATIONSHIP

BACKGROUND OF THE INVENTION

The present invention relates to an apparatus which is used to retain bone portions, such as vertebrae of a spinal column, in a desired spatial relationship.

A known apparatus for retaining vertebrae of a spinal column in a desired spatial relationship includes a longitudinal plate extendable along the spinal column. The plate includes a plurality of elongate slots extending along a longitudinal axis of the plate. A fastener has a first end portion that engages a vertebrae of the spinal column and a second end portion which extends through one of the slots in the plate. A nut threadably engages the second end portion of the fastener and clamps the plate to the fastener.

The elongate slots in the plate are defined by a plurality of frustoconical recesses which are engaged by a surface of the nut. The recesses define a plurality of nests which prevent movement of the plate relative to the fastener. The nests define a plurality of locations for receiving the fastener. Accordingly, there are only a certain number of positions for the fastener relative to the plate and infinite adjustments of the position of the plate relative to the fastener cannot be achieved.

The known longitudinal plates have a uniform stiffness along their length to prevent stress from being applied to healthy and deformed vertebrae to which the plate is connected. However, low stress deformation of bone is important in bone remodeling since the bone remodels to support applied loads. When the known plates are connected to bone, the surrounding bone of healthy vertebrae is shielded from applied stresses and the bone of the healthy vertebrae resorbs. Furthermore, the known stiff plates cause increased loads to be applied to a spine disk between the uppermost vertebra that the plate is connected to and an adjacent vertebra to which the plate is not connected. These increased loads cause degeneration of the disk.

SUMMARY OF THE INVENTION

In accordance with the present invention, an apparatus for retaining bone portions, such as vertebrae of a spinal column, in a desired spatial relationship includes a longitudinal plate extendable along the bone portions. The plate has a first major side surface for facing the bone portions and a second major side surface for facing away from the bone portions. A fastener has a first end portion engageable with a bone portion. A connecting means connects the plate to the fastener in any one of an infinite number of positions along a longitudinal axis of the plate. The connecting means includes surface means for defining a recess for receiving a portion of the plate. The surface means defining the recess has an interference fit with the portion of the plate received in the recess. A nut threadably engages the second end portion of the fastener to apply a force to the connecting member to cause the interference fit between the plate and the recess.

In a preferred embodiment of the invention, the first major side of the plate is spaced from the second major side surface a first distance at a first location along the longitudinal axis of the plate. The first major side surface is spaced from the second major side surface a second distance which is less than the first distance at a second location along the axis of the plate. Accordingly, the plate has a relatively flexible portion that can be connected to the uppermost vertebra that the plate is to be connected to. The relatively flexible portion helps prevent bone resorption and disk degeneration.

BRIEF DESCRIPTION OF THE DRAWINGS

The foregoing and other features of the present invention will become apparent to one skilled in the art upon consideration of the following description of the preferred embodiments of the invention with reference to the accompanying drawings, wherein.

DESCRIPTION OF A PREFERRED EMBODIMENT OF THE INVENTION

A pair of surgically implantable longitudinal plates 10 (FIG. 1) for maintaining bone portions, such as vertebrae of a spinal column, are connected with several vertebrae V of a spinal column 12 by fasteners 20. Each plate 10 can be curved to conform to a desired curvature of the spinal column 12, as illustrated in FIG. 2. Although the plates are shown maintaining three vertebrae in a desired spatial relationship, they may be used to maintain any number of vertebrae in a desired spatial relationship. Also, the plates may be used to maintain bone portions, such as portions of a broken bone, in a desired spatial relationship.

Figure 3:
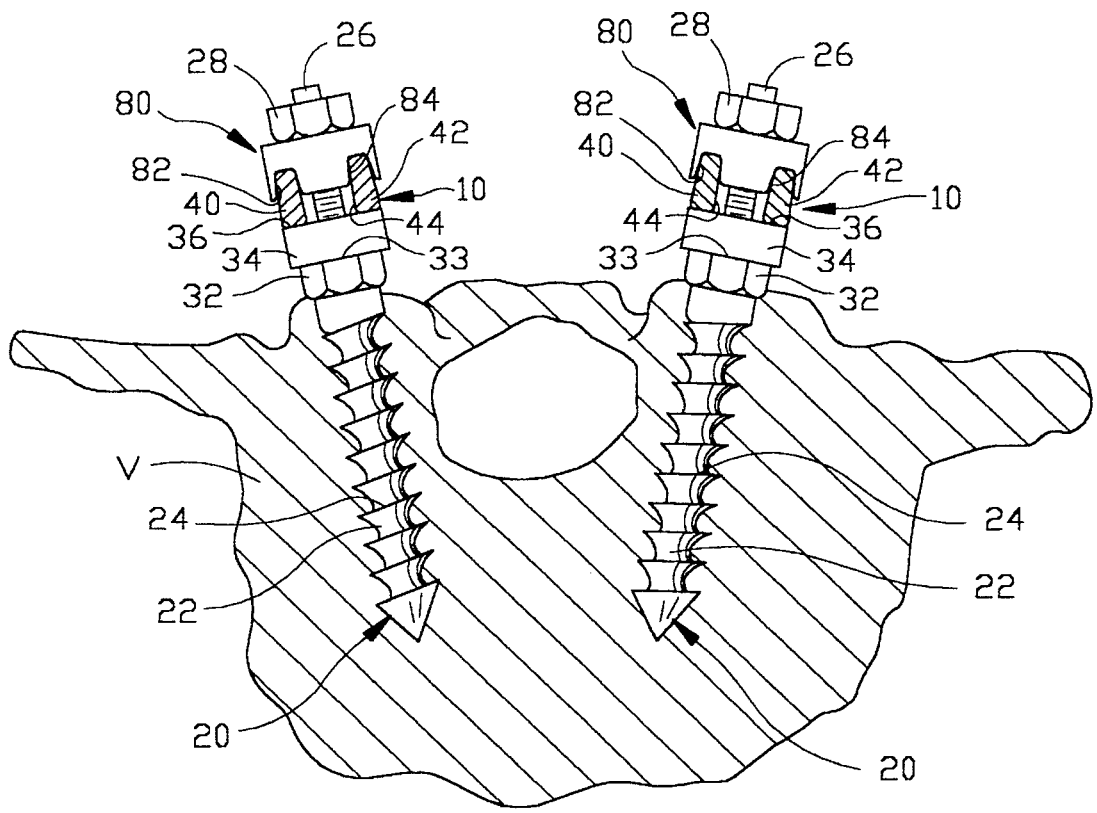
FIG. 3 is a sectional view, taken generally along the line 3—3 of FIG. 1, illustrating the manner in which fasteners are used to connect longitudinal plates with a vertebra.

The plates 10 are connected to respective vertebrae V by fasteners 20 (FIG. 3) made of suitable biocompatible material, such as titanium or stainless steel. Each of the fasteners 20 has a threaded inner end portion 22 having a coarse helical thread convolution 24 which engages the vertebra V. An outer end portion 26 of the fastener 20 is provided with a relatively fine thread which engages an internal thread convolution on a nut 28 preferably made of a suitable biocompatible material, such as titanium or stainless steel.

Wrenching flats (not shown) are provided on the outermost end of the outer end portion 26 of the fastener 20. Torque is applied to these wrenching flats to turn the relatively coarse helical thread convolution 24 into the vertebra V. Once the fastener 20 has been connected to the vertebra and the plate 10, the outer end portion of the fastener may be cut away to minimize the overall length of the fastener.

An intermediate portion 32 of the fastener has a flat outer side surface 33 which abuttingly engages a spacer washer 34. When the clamp nut 28 is tightened, the plate 10 is securely clamped against a flat outer side surface 36 of the washer 34, which is connected with the fastener 20. The washer 34 spaces the plate 10 away from the vertebra V and may have any desired thickness or not be used at all. If the washer 34 is not used, the plate is clamped against the surface 33 of the intermediate portion 32 of the fastener 20.

Although it is contemplated that the fastener 20 could have many different constructions, it is preferred to construct the fastener 20 in accordance with U.S. Pat. No. 4,854,311 which is assigned to the assignee of the present invention.

Each of the plates 10 has a length which is at least sufficient to enable the plate to span at least two of the vertebrae V. In the embodiment of the invention illustrated in FIG. 1, the plates 10 span three vertebrae V. Of course, the length of the plates 10 in any particular installation will depend upon the condition to be corrected and the number of vertebrae V to be held in a desired spatial relationship relative to each other by the bone plates.

Figure 1:
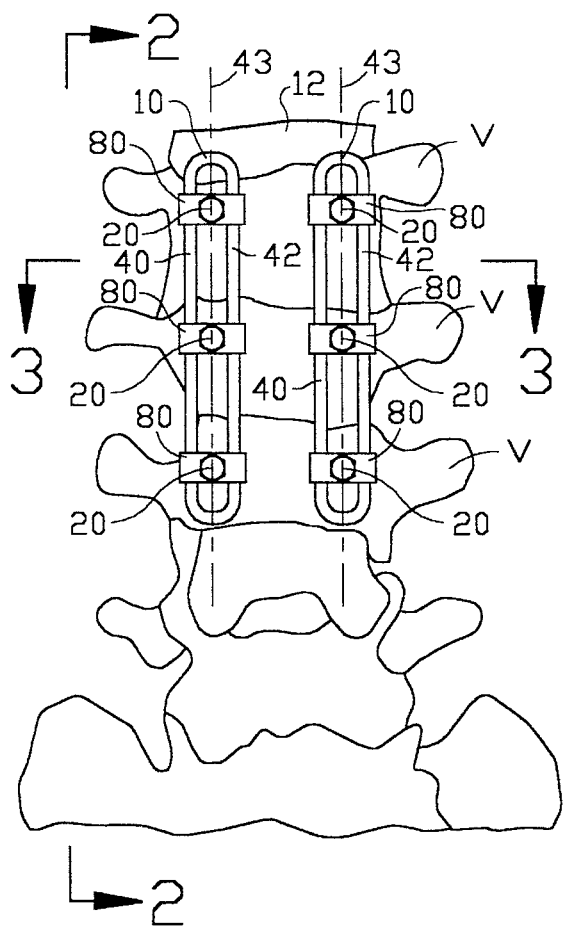
FIG. 1 is a posterior view of a human spinal column in which an apparatus constructed in accordance with the present invention has been implanted.
Figure 2:
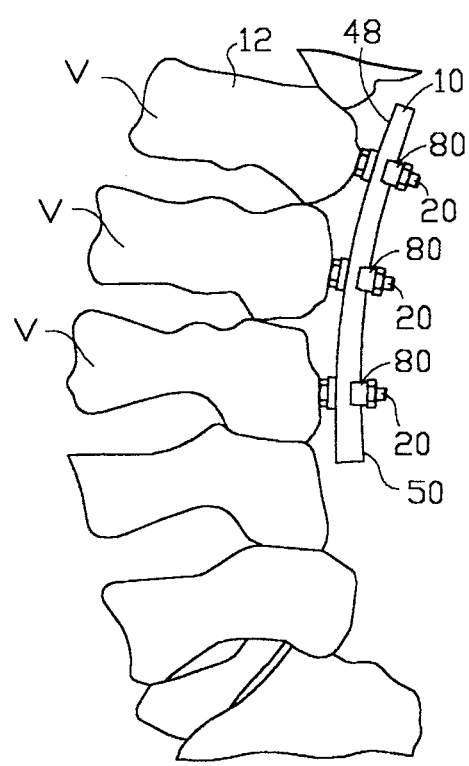
FIG. 2 is a left lateral view, taken generally along the line 2—2 of FIG. 1.

Each of the plates 10 is identical and includes first and second longitudinally extending side portions 40 and 42 (FIG. 1). The side portions 40 and 42 extend parallel to each other and to a longitudinal axis 43 of the plate 10. The first and second side portions 40 and 42 define a slot 44 in the plate 10 that extends along the axis 43.

Figure 5:
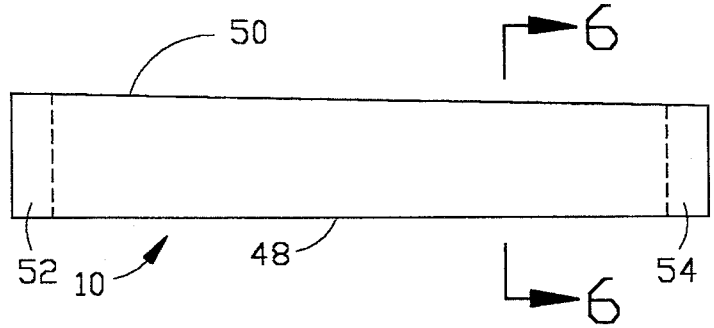
FIG. 5 is an enlarged side view of a longitudinal plate of FIG. 1.

The plate 10 (FIGS. 2 and 5) has a lower surface 48 for facing the vertebrae V and an upper surface 50 for facing away from the vertebrae V. Preferably, the surfaces 48 and 50 are spaced apart a first distance adjacent a first end 52 (FIG. 5) of the plate 10 and spaced apart a second distance, less than the first distance, adjacent a second end 54 of the plate. The plate 10 tapers from the first end 52 to the second end 54. Accordingly, the plate 10 is more flexible adjacent the end 54 than adjacent the end 52 to prevent stress shielding of the vertebrae connected with the end 54 and degeneration of a spine disk (not shown) located between the uppermost vertebra connected with the end 54 and the adjacent vertebra not connected to the plate. It is contemplated that the plate 10 could taper from a central portion of the plate to both ends of the plate to prevent stress shielding of the vertebrae connected to both ends of the platen Also, the upper and lower surfaces may extend parallel to each other so the plate does not taper at all and has a uniform stiffness throughout its length.

Figure 6:
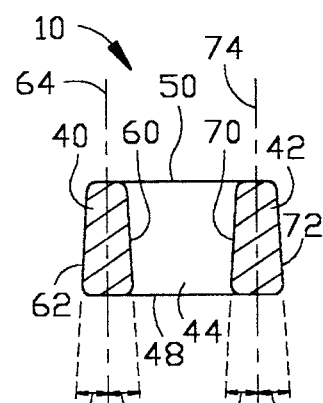
FIG. 6 is a sectional view of the longitudinal plate, taken generally along the line 6—6 of FIG. 5.

The side portion 40 (FIG. 6) of the plate 10 has an inner surface 60 defining the slot 44 and an outer surface 62 located laterally from the inner surface of the side portion 40. The inner surface 60 of the first side portion 40 extends at an angle A relative to a line 64 extending substantially perpendicular to the lower surface 48. The outer surface 62 of the side portion 40 extends at an angle B relative to the line 64. Preferably, angles A and B are equal and are approximately 2.4°. Therefore, the inner and outer surfaces 60 and 62 extend at an angle of approximately 4.8° relative to each other.

The side portion 42 of the plate 10 has an inner surface 70 defining the slot 44 and an outer surface 72 located laterally from the inner surface 70 of the side portion 42. The inner surface 70 of the second side portion 42 extends at an angle C relative to a line 74 extending substantially perpendicular to the lower side surface 48. The outer surface 72 of the second side portion 42 extends at an angle D relative to the line 74. Preferably, angles C and D are equal and are approximately 2.4°. Therefore, the inner and outer surfaces 70 and 72 extend at an angle of approximately 4.8° relative to each other. Also, the outer surfaces 62 and 72 extend at an angle relative to each other.

A connecting member 80 (FIG. 1) connects the fastener 20 to the plate 10 in any one of an infinite number of positions along the slot 44. The connector member 80 (FIG. 3) has first and second recesses 82 and 84 for receiving the first and second side portions 40 and 42 of the plate 10. The first and second recesses 82 and 84 have an interference fit with the first and second side portions 40 and 42 of the plate 10.

Figure 4:
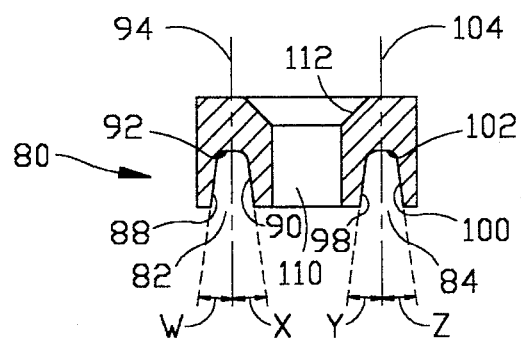
FIG. 4 is an enlarged sectional view of a connector member of FIG. 1.

First and second side surfaces 88 and 90 (FIG. 4) and a bottom surface 92 extending between the first and second side surfaces define the recess 82. The first side surface 88 extends at an angle W relative to a line 94 extending substantially perpendicular to the bottom surface 92 of the recess 82. The second side surface 90 extends at an angle X relative to the line 94. Preferably, the angles W and X are equal and are approximately 2.5°. Therefore, the side surfaces 88 and 90 extend at an angle of approximately 5° relative to each other.

First and second side surface 98 and 100 and a bottom surface 102 extending between the first and second side surfaces 98 and 100 define the recess 84. The first side surface 98 of the recess 84 extends at an angle Y relative to a line 104 extending substantially perpendicular to the bottom surface 102 of the recess 84. The second side surface 100 of the recess 84 extends at an angle Z relative to the line 104. Preferably, the angles Y and Z are equal and are approximately 2.5°. Therefore, the first and second side surfaces 98 and 100 of the recess 84 extend at an angle of approximately 5° relative to each other.

The connecting member 80 includes an opening 110 through which the second end portion 26 of the fastener extends. The opening 110 is located between the recesses 82 and 84. The connector member 80 includes a frustoconical recess 112 for receiving a frustoconical portion of the nut 28.

The first side portion 40 (FIG. 6) of the plate 10 has a width measured from the inner side surface 60 to the outer side surface 62 and along the upper surface 50. The bottom surface 92 (FIG. 4) of the recess 82 has a width measured from the first side surface 88 to the second side surface 90. Preferably, the width of the first side portion 40 measured along the upper surface 50 is greater than the width of the bottom surface 92 of the recess 82 to cause an interference fit.

The second side portion 42 (FIG. 6) of the plate 10 has a width measured from the inner side surface 70 to the outer side surface 72 and along the upper surface 50. The bottom surface 102 (FIG. 4) of the recess 84 has a width measured from the first side surface 98 to the second side surface 100. Preferably, the width of the second side portion 42 measured along the upper surface 50 is greater than the width of the bottom surface 102 of the recess 84 to cause an interference fit.

When the plates 10 are to be mounted on a spinal column 12, a plurality of fasteners 20 are connected to the vertebrae. After the plates 10 have been bent to the desired configuration, the plates 10 are placed on the fasteners 20. If washers 34 are to be used, the washers are placed on the fasteners 20 before placing the plates 10 on the fasteners. The plate 10 is preferably placed with the more flexible end 54 toward the head of the patient and connected with healthy vertebrae. The plates 10 can be positioned along the fasteners 20 with the fasteners in any one of an infinite number of positions along the slot 44.

Once the plates 10 have been positioned relative to the fasteners 20, connecting members 80 are placed on the fasteners with the recesses 82 and 84 receiving side portions 40 and 42 of the plates 10. Nuts 28 are threaded onto fasteners 20 to cause the interference fit between the recesses 82 and 84 and the side portions 40 and 42 and fix the positions of the plates relative to the fasteners. The nuts 28 cause the connecting members 80 to clamp the lower side surfaces 48 of the plates 10 against surfaces 36 of the washers 34 if the washers are used, or against surfaces 33 of the fasteners 20 if the washers are not used.

From the above description of the invention, those skilled in the art will perceive improvements, changes and modifications. Such improvements, changes and modifications within the skill of the art are intended to be covered by the appended claims.

Having described the invention, the following is claimed:

1. An apparatus for retaining bone portions in a desired spatial relationship, said apparatus comprising:

a longitudinal plate extendable along the bone portions, said plate including a first major side surface for facing the bone portions and a second major side surface for facing away from the bone portions;

a fastener having a first end portion engageable with a bone portion and a second end portion;

connecting means for connecting said plate to said fastener in any one of an infinite number of positions along a longitudinal axis of said plate, said connecting means including surface means for defining a recess for receiving a portion of said plate, said surface means defining said recess having an interference fit with said portion of said plate received in said recess; and means engageable with said second end portion of said fastener for applying a force to cause the interference fit between said plate and said recess.

2. An apparatus as set forth in claim 1 wherein said surface means defining said recess includes first and second side surfaces and a bottom surface extending between said first and second side surfaces, said first side surface extending at an angle relative to said second side surface.

3. An apparatus as set forth in claim 2 wherein said first and second side surfaces extend at an angle to a line extending substantially perpendicular to said bottom surface.

4. An apparatus as set forth in claim 1 wherein said plate includes first and second longitudinally extending laterally outer surfaces extending between said first and second major side surfaces; said first and second laterally outer surfaces extending at an angle relative to each other.

5. An apparatus as set forth in claim 4 wherein said surface means defining said recess includes first and second side surfaces and a bottom surface extending between said first and second side surfaces, said first and second side surfaces extending at an angle relative to each other.

6. An apparatus as set forth in claim 1 wherein said plate includes first and second side portions extending parallel to each other and the longitudinal axis, said first and second side portions connecting said first and second major side surfaces, said first and second side portions defining an elongate slot extending along the longitudinal axis of said plate and intersecting said first and second major side surfaces, said second end portion of said fastener being extendable through said slot, said recess in said connecting means receiving said first side surface, said connecting means including surface means for defining a second recess for receiving said second side portion of said plate, said surface means defining said first and second recesses having an interference fit with said first and second side portions, respectively.

7. An apparatus as set forth in claim 6 wherein said surface means defining said first recess includes first and second side surfaces and a bottom surface extending between said first and second side surfaces, said first side surface of said first recess extending at an angle relative to said second side surface of said first recess, said surface means defining said second recess including first and second side surfaces and a bottom surface extending between said first and second side surfaces, said first side surface of said second recess extending at an angle relative to said second side surface of said second recess.

8. An apparatus as set forth in claim 7 wherein said first and second side surfaces of said first recess extend at an angle relative to a first line extending substantially perpendicular to said bottom surface of said first recess, said first and second side surfaces of said second recess extending at an angle relative to a second line extending substantially perpendicular to said bottom surface of said second recess.

9. An apparatus as get forth in claim 8 wherein said first and second side surfaces of said first recess extend at an angle of approximately 5° relative to each other, said first and second side surfaces of said second recess extending at an angle of approximately 5° relative to each other.

10. An apparatus as set forth in claim 6 wherein said first side portion of said plate has an inner surface defining said slot and an outer surface located laterally from said inner surface of said first side portion, said inner surface of said first side portion extending at an angle relative to said outer surface of said first side portion, said second side portion of said plate having an inner surface defining said slot and an outer surface located laterally from said inner surface of said second side portion, said inner surface of said second side portion extending at an angle relative to said outer surface of said second side portion.

11. An apparatus as set forth in claim 10 wherein said inner and outer surfaces of said first side portion extend at an angle relative to a first line extending substantially perpendicular to at least one of said first and second major side surfaces, said inner and outer surfaces of said second side portion extending at an angle relative to a second line extending substantially perpendicular to at least one of said first and second major side surfaces.

12. An apparatus as set forth in claim 11 wherein said inner and outer surfaces of said first side portion extend at an angle of approximately 4.8° relative to each other, said inner and outer surfaces of said second side portion extending at an angle of approximately 4.8° relative to each other.

13. An apparatus as set forth in claim 10 wherein said surface means defining said first recess includes first and second side surfaces and a bottom surface extending between said first and second side surfaces, said first side surface of said first recess extending at an angle relative to said second side surface of said first recess, said surface means defining said second recess including first and second side surfaces and a bottom surface extending between said first and second side surfaces, said first side surface of said second recess extending at an angle relative to said second side surface of said second recess.

14. An apparatus as set forth in claim 13 wherein said inner and outer surfaces of said first side portion of said plate extend at an angle relative to each other that is less than the angle at which said first and second side surfaces of said first recess extend relative to each other, said inner and outer surfaces of said second side portion of said plate extending at an angle relative to each other that is less than the angle which said first and second side surfaces of said second recess extend relative to each other.

15. An apparatus as set forth in claim 1 wherein said connecting means includes a connecting member including said surface means defining said recess, said connecting member clamping one of said first and second major side surfaces of said plate against a substantially flat surface connected with said fastener.

16. An apparatus as set forth in claim 15 wherein said connecting member includes second surface means for defining an opening through which said second end portion of said fastener is extendable.

17. An apparatus as set forth in claim 1 wherein said surface means defining said recess includes first and second side surfaces and a bottom surface extending between said first and second side surfaces, said first and second side surfaces being spaced apart a distance measured substantially parallel to said bottom surface which varies along said first and second side surfaces as they extend from said bottom surface, said portion of said plate received in said recess having first and second surfaces extending between said first and second major side surfaces, said first and second surfaces being spaced apart a distance, measured along one of said first and second major side surfaces, at least equal to a minimum distance between said first and second side surfaces of said recess.

18. An apparatus as set forth in claim 1 wherein said first and second major side surfaces of said plate are spaced apart from each other a first distance at one location along the longitudinal axis of said plate and spaced apart a second distance which is less than the first distance at a second location along the longitudinal axis of said plate.

19. An apparatus as set forth in claim 18 wherein said plate tapers along its length from a first end portion corresponding to said one location to a second end portion corresponding to said second location.

20. An apparatus for retaining bone portions in a desired spatial relationship, said apparatus comprising:

a longitudinal plate extendable along the bone portions, said plate including a first major side surface for facing the bone portions, a second major side surface for facing away from the bone portions, and an elongate slot extending along a longitudinal axis of said plate and intersecting said first and second major side surfaces;

a fastener having a first end portion engageable with a bone portion and a second end portion extendable through said slot in said plate;

a connecting member for connecting said plate to said fastener in any one of an infinite number of positions along said slot, said connecting member including surface means for defining a recess for receiving a portion of said plate, said connecting member clamping one of said first and second major side surfaces of said plate against a substantially flat surface connected with said fastener; and means engageable with said second end portion of said fastener for applying a clamping force to said connecting member.

21. An apparatus as set forth in claim 20 wherein said plate includes first and second side portions extending parallel to each other and the longitudinal axis, said first and second side portions connecting said first and second major side surfaces and defining said slot in said plate, said recess in said connecting member receiving said first side portion, said connecting member including second surface means for defining a second recess for receiving said second side portion of said plate, said surface means defining said first and second recesses having an interference fit with said first and second side portions, respectively.

22. An apparatus as set forth in claim 21 wherein said surface means defining said first recess includes first and second side surfaces and a bottom surface extending between said first and second side surfaces, said first and second side surfaces of said first recess extending at an angle relative to a line extending substantially perpendicular to said bottom surface of said first recess, said surface means defining said second recess including first and second side surfaces and a bottom surface extending between said first and second side surfaces, said first and second side surfaces of said second recess extending at an angle relative to a line extending substantially perpendicular to said bottom surface of said second recess.

23. An apparatus as set forth in claim 22 wherein said first side portion of said plate has an inner surface defining said slot and an outer surface located laterally from said inner surface of said first side portion, said inner and outer surfaces of said first side portion extending at an angle relative to a first line extending substantially perpendicular to at least one of said first and second major side surfaces, said second side portion of said plate having an inner surface defining said slot and an outer surface located laterally from said inner surface of said second side portion, said inner and outer surfaces of said second side portion extending at an angle relative to a second line extending substantially perpendicular to at least one of said first and second major side surfaces.

24. An apparatus as set forth in claim 20 wherein said first and second major side surfaces of said plate are spaced apart from each other a first distance at one location along the longitudinal axis of said plate and spaced apart a second distance which is less than the first distance at a second location along the longitudinal axis of said plate.

25. An apparatus as set forth in claim 20 wherein said connecting member includes second surface means for defining an opening through which said second end portion of said fastener is extendable.

26. An apparatus as set forth in claim 25 wherein said second surface means defining said opening in said connecting member defines a frustoconical recess for receiving a frustoconical portion of said means for applying the clamping force.

27. An apparatus for retaining bone portions in a desired spatial relationship, said apparatus comprising:

a longitudinal plate extendable along the bone portions, said plate including a first major side surface for facing the bone portions and a second major side surface for facing away from the bone portions, said first and second major side surfaces of said plate being spaced apart from each other a first distance at one location along a longitudinal axis of said plate and spaced apart a second distance which is less than the first distance at a second location along the longitudinal axis of said plate;

a fastener having a first end portion engageable with a bone portion and a second end portion; and connecting means for connecting said plate to said second end portion of said fastener.

28. An apparatus as set forth in claim 27 wherein said plate includes first and second side portions extending parallel to each other and the longitudinal axis, said first and second side portions connecting said first and second major side surfaces, said first and second side portions defining an elongate slot extending along the longitudinal axis of said plate and intersecting said first and second major side surfaces, said second end portion of said fastener being extendable through said slot, said connecting means including surface means for defining first and second recesses for receiving said first and second side portions of said plate, respectively, said surface means defining said first and second recesses having an interference fit with said first and second side portions.

29. An apparatus as set forth in claim 28 wherein said surface means defining said first recess includes first and second side surfaces and a bottom surface extending between said first and second side surfaces and for facing toward said second major side surface of said plate, said first and second side surfaces of said first recess extending at an angle relative to a line extending substantially perpendicular to said bottom surface of said first recess, said surface means defining said second recess including first and second side surfaces and a bottom surface extending between said first and second side surfaces and for facing said second major side surface of said plate, said first and second side surfaces of said second recess extending at an angle relative to a line extending substantially perpendicular to said bottom surface of said second recess.

30. An apparatus as set forth in claim 29 wherein said first side portion of said plate has a longitudinally extending inner surface defining said slot and a longitudinally extending outer surface located laterally from said inner surface of said first side portion, said inner and outer surfaces of said first side portion extending at an angle relative to a first line extending substantially perpendicular to at least one of said first and second major side surfaces, said second side portion of said plate having a longitudinally extending inner surface defining said slot and a longitudinally extending outer surface located laterally from said inner surface of said second side portion, said inner and outer surfaces of said second side portion extending at an angle relative to a second line extending substantially perpendicular to at least one of said first and second major side surfaces.

31. An apparatus as set forth in claim 28 wherein said first and second side surfaces of said first recess are spaced apart a distance measured substantially parallel to said bottom surface of said first recess which varies along said first and second side surfaces as they extend from said bottom surface, said first side portion of said plate having an inner surface defining said slot and an outer surface located laterally from said inner surface of said first side portion, said inner and outer surfaces of said first side portion being spaced apart a distance measured along said second major side surface which is at least equal to a minimum distance between said first and second side surfaces of said first recess, said first and second side surfaces of said second recess being spaced apart a distance measured substantially parallel to said bottom surface of said second recess which varies along said first and second side surfaces as they extend from said bottom surface, said second side portion of said plate having an inner surface defining said slot and an outer surface located laterally from said inner surface of said second side portion, said inner and outer surfaces of said second side portion being spaced apart a distance measured along said second major side surface which is at least equal to a minimum distance between said first and second side surfaces of said second recess.

32. An apparatus for retaining bone portions in a desired spatial relationship, said apparatus comprising:

a longitudinal plate extendable along the bone portions, said plate including a first major side surface for facing the bone portions, a second major side surface for facing away from the bone portions, and an elongate slot extending along a longitudinal axis of said plate and intersecting said first and second major side surfaces, said plate including first and second side portions extending parallel to each other and the longitudinal axis, said first side portion of said plate having an inner surface defining said slot and an outer surface located laterally from said inner surface of said first side portion, said inner and outer surfaces of said first side portion extending at an angle relative to a first line extending substantially perpendicular to at least one of said first and second major side surfaces, said second side portion of said plate having an inner surface defining said slot and an outer surface located laterally from said inner surface of said second side portion, said inner and outer surfaces of said second side portion extending at an angle relative to a second line extending substantially perpendicular to at least one of said first and second major side surfaces;

a fastener having a first end portion engageable with a bone portion and a second end portion extendable through said slot in said plate;

a connecting member for connecting said plate to said fastener in any one of an infinite number of positions along said slot, said connecting member clamping said plate against a substantially flat surface connected with said fastener, said connecting member including surface means for defining first and second recesses for receiving said first and second side portions of said plate, respectively, said surface means defining said first recess including first and second side surfaces and a bottom surface extending between said first and second side surfaces, said first and second side surfaces of said first recess extending at an angle relative to a line extending substantially perpendicular to said bottom surface of said first recess, said surface means defining said second recess including first and second side surfaces and a bottom surface extending between said first and second side surfaces, said first and second side surfaces of said second recess extending at an angle relative to a line extending substantially perpendicular to said bottom surface of said second recess, said surface means defining said first and second recesses having an interference fit with said first and second side portions of said plate; and means engageable with said second end portion of said fastener for applying a force to said connecting member to cause the interference fit between said first and second side portions of said plate and said first and second recesses of said connecting member.

33. An apparatus as set forth in claim 32 wherein said first and second major side surfaces of said plate are spaced apart from each other a first distance at one location along the longitudinal axis of said plate and spaced apart a second distance which is less than the first distance at a second location along the longitudinal axis of said plate.

34. An apparatus as set forth in claim 32 wherein said first and second side surfaces of said first recess extend at an angle of approximately 5° relative to each other, said first and second side surfaces of said second recess extending at an angle of approximately 5° relative to each other, said inner and outer surfaces of said first side portion of said plate extending at an angle of approximately 4.8° relative to each other, said inner and outer surfaces of said second side portion of said plate extending at an angle of approximately 4.8° relative to each other.

35. An apparatus as set forth in claim 32 wherein said connecting member includes second surface means for defining an opening through which said fastener is extendable, said opening being located between said first and second recesses in said connecting member.

* * * * *